United States Patent [19]

Nag et al.

[11] Patent Number: 6,127,338
[45] Date of Patent: Oct. 3, 2000

[54] ORALLY ACTIVE FRACTION OF MOMORDICA CHARANTIA, ACTIVE PEPTIDES THEREOF, AND THEIR USE IN THE TREATMENT OF DIABETES

[75] Inventors: Bishwajit Nag, Fremont; Satyanarayana Medicherla, Sunnyvale; Somesh D. Sharma, Los Altos, all of Calif.

[73] Assignee: Calyx Therapeutics, Inc., Hayward, Calif.

[21] Appl. No.: 09/053,617

[22] Filed: Apr. 1, 1998

Related U.S. Application Data

[63] Continuation-in-part of application No. 08/850,855, May 2, 1997, abandoned, which is a continuation-in-part of application No. 08/831,039, Apr. 1, 1997, abandoned.

[51] Int. Cl.[7] .......................... A61K 38/04; A61K 38/06; A61K 38/10; C07K 7/06; C07K 7/08

[52] U.S. Cl. ................................ 514/13; 514/15; 514/16; 530/326; 530/327; 530/329

[58] Field of Search ........................ 424/195.1; 530/303, 530/327, 328, 329, 330, 331; 514/2, 3, 14–18

[56] References Cited

U.S. PATENT DOCUMENTS

| | | | |
|---|---|---|---|
| 3,817,837 | 6/1974 | Rubenstein et al. | 435/7.9 |
| 3,850,752 | 11/1974 | Schuurs et al. | 435/7.93 |
| 3,853,914 | 12/1974 | Goldstein et al. | 548/542 |
| 3,905,654 | 9/1975 | Tribe | 303/115.4 |
| 3,945,988 | 3/1976 | Khannet al. | 530/305 |
| 4,043,989 | 8/1977 | Schneider et al. | 530/363 |
| 4,069,105 | 1/1978 | Singh et al. | 530/363 |
| 4,156,081 | 5/1979 | Singh et al. | 544/271 |
| 4,368,149 | 1/1983 | Masuho et al. | 530/391.9 |
| 4,985,248 | 1/1991 | Liu | 424/195.1 |
| 5,086,043 | 2/1992 | Liu | 514/25 |
| 5,098,710 | 3/1992 | Liu | 424/195.1 |

OTHER PUBLICATIONS

Stahl et al. Biochem. (1993) 32: 1991–2002.
Rudinger "Peptide Hormones," Parsons J.A., editor. (1976) (University park press: Baltimore, MD) p. 1–7.
Akhtar et al., (1981) "Effect of Momordica charantia on Blood Glucose Level of Normal and Alloxan–diabetic Rabbits," *Planta Med.* 42: 205–212.
Ali et al., (1993) "Studies on Hypoglycemic Effects of Fruit Pulp, Seed, and Whole Plant of *Momordica charantia* on Normal and Diabetic Model Rats," *Planta Med.* 59: 408–412.
Aslam et al. (1979) "Interaction Between curry Incredient (Karela) and Drug (Chlorpropamide)" *Lancet* I:607.
Baldwa et al. (1977) "Clinical Trial in Patients with Diabetes Mellitus of an Insulin–like Compound Obtained from Plant Source," *Upsala J. Med. Sci.* 82:39–41.
Di Colo (1992) "Controlled drug release from implantable matrices based on hydrophobic polymers," *Biomaterials* 13: 850–856.
Driscoll et al. (1993) "Two–dimensional Nuclear Magnetic Resonance Analysis of a Labeled Peptide Bound to a Class II Major Histocompatibility Complex Molecule," *J. Mol. Bio.* 232:342–350.
Dubey, D.K., et al. (1987) "Hypoglycaemic and Antihyperglycaemic Effects of *Momordica* Charantia Seed Extracts in Albino Rats," *Fitoterapia* 58(6):387–39.
El–Gengaihi, S., et al. (1996) "Chemical and Biological Investigation of Polypeptides of Momordica and Luffa Spp. Fam. Cucurbitaceae," *Bull. Natl. Res. Cent.* (Egypt) 21(3):269–276.
Hales & Randle, (1963) "Immunoassay of Insulin with Insulin–Antibody Precipitate," *Biochem. J.* 88:137.
Harrison's "Principles of Internal Medicine", 11th ed., Braunwald et al. ed., *McGraw Hill Book Co. NY* 1987.
Heller, "Biodegradable Polymers in Controlled Drug Delivery," *CRC Critical Reviews in Therapeutic Drug Carrier Systems*, vol. 1, CRC Press, Boca Raton, FL 1987, pp. 39–90.
Kadish et al. (1968) "A New and Rapid Method for the Determination of Glucose by Measuraement of Rate of Oxygen Consumption," *Clin. Chem.* 14: 116.
Karunanayake, E.H., et al. (1984) "Oral Hypoglycaemic Activity of Some Medicinal Plants of SRI Lanka," *J. Ethnopharmacol.* 11(2):223–232.
Khanna, P., et al. (1979) "A Hypoglycemic Polypeptide From Vegetable Source with an Alternate Mode of Action," *J. Natural Products* 42(6):684.
Khanna et al. "Hypoglycemic Activity of Polypeptide–p from a Plant Source," 20th Annual Meeting of the American Society of Pharmacoloby, Purdue University, West Lafayette, Jul. 29–Aug. 3, 1979.
Ng,Ph.D. et al., "Acid–Ethanol Extractable Compounds from Fruits and Seeds of the Bitter Gourd Momordica Charantia: Effects on Lipid Metabolism in Isolated Rat Adipocytes," *The American J. of Chinese Medicine*, vol. 15, No. 1–2, 31–42, 1987.
Lei, Q., et al. (1985) "Influence of Balsam Pear (The Fruit of Momordica Charanti a L.) On Blood Sugar Level." *J. Tradit. Chin. Med.* 5(2):99–106.
Pugazhenthi, S., et al. (1996) "Purification of Three Orally Active Hypoclycemic Compounds Kakara 1B, 111a, and 111b, from the Unripe Fruits of Momordica charantia" Linn (Bitter Gourd) *Indian J. Clin. Biochem.* 11(2):115–119.

(List continued on next page.)

*Primary Examiner*—Jon P. Weber
*Attorney, Agent, or Firm*—Fish & Richardson P.C.

[57] ABSTRACT

A water soluble extract of *M.charantia* named MC6, methods for its preparation and methods for its use in the treatment of hyperglycemic disorders are provided. The active MC6 is characterized by moving as a single band on SDS-PAGE having a molecular weight of less than 10 kDal, and by comprising three peptides. Also provided is a peptide component of MC6 named MC6.1, as well as analogues and mimetics thereof. The active MC6, MC6.1, MC6.2, and MC6.3 exhibit hypoglycemic activity, even following oral administration. Also provided are methods of using the active agents to treat hyperglycemic disorders, particularly diabetes, where the active agents are preferably orally administered.

5 Claims, 11 Drawing Sheets

OTHER PUBLICATIONS

Raman et al. "Anti–diabetic properties and phytochemistry of Momordica charantia L. (Cucurbitaceae)," *Phytomedicine*, vol. 2, No. 4, 349–362, 1996.

Reza–Ul–Jalil, et al. (1986) "Hypoglycemic Activities of the Glycosides of Momordica Cochinchinensis," *J. Bangladesh Acad. Sci* 10(1):25–30.

Sambrook et al. (1989) *Molecular cloning: A Laboratory Manual*, pp V–XXXII CSHL Press, Cold Spring Harbor, NY 2nd edition.

Sarkar et al. (1996) "Demonstration of the Hypoglycemic Action of Momordica Charantia in a Validated Animal Model of Diabetes," *Pharmacol. Res.* 33: 1–4.

Shibib et al., (1993) *Biochem. J.* 292: 267–270.

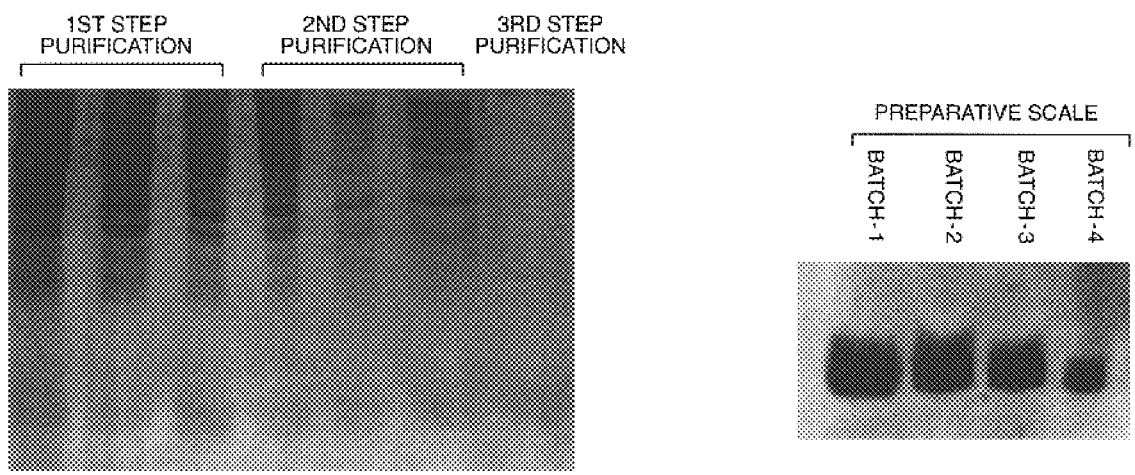
FIG._1A
FIG._1B

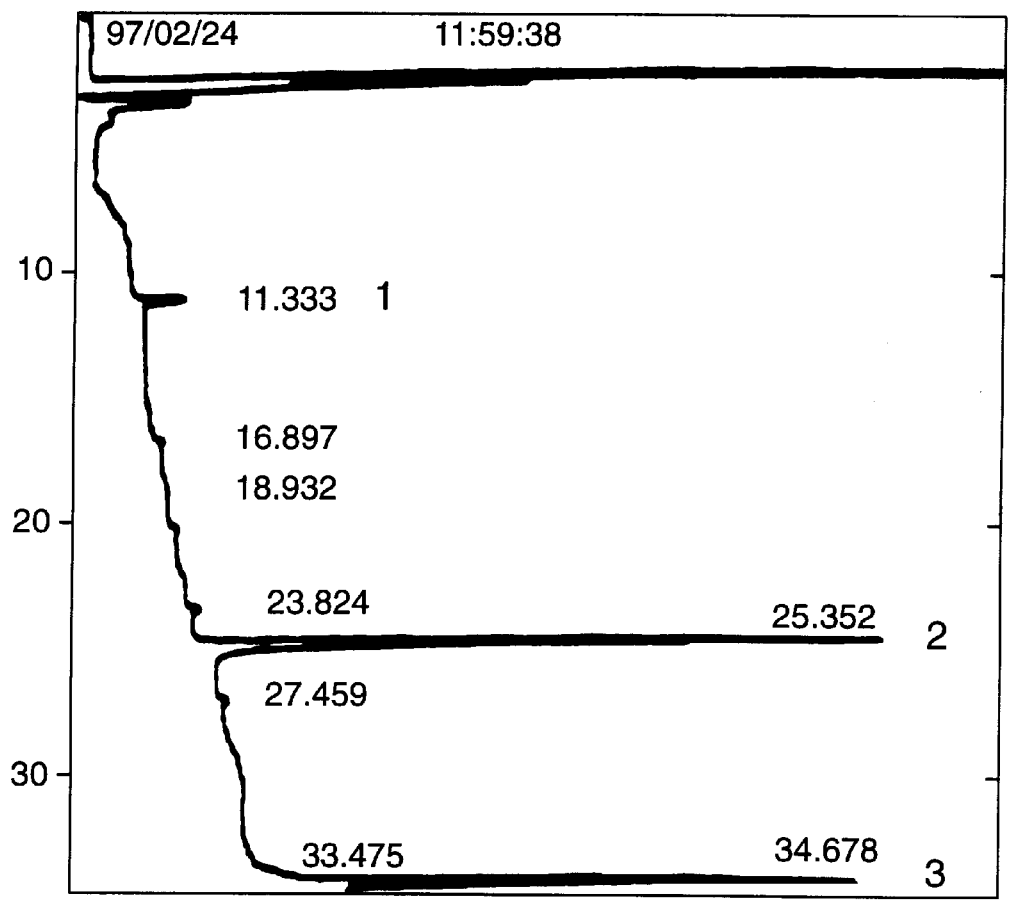
FIG._1C

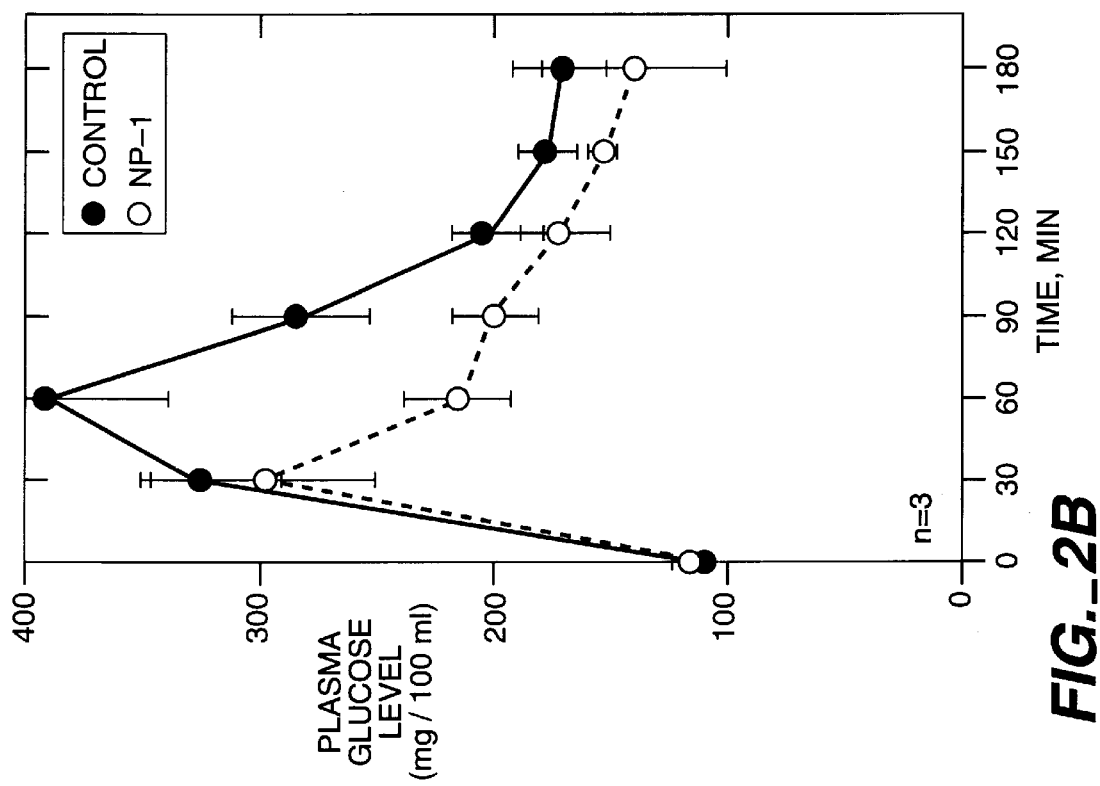
FIG._2B
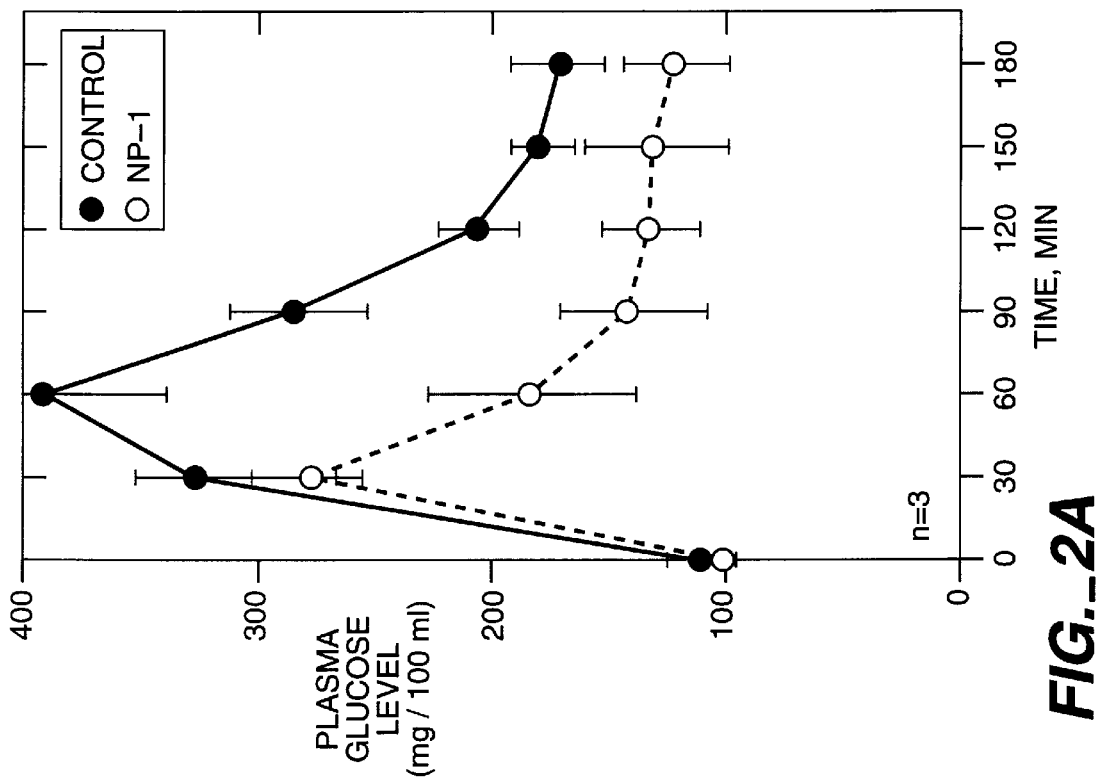
FIG._2A

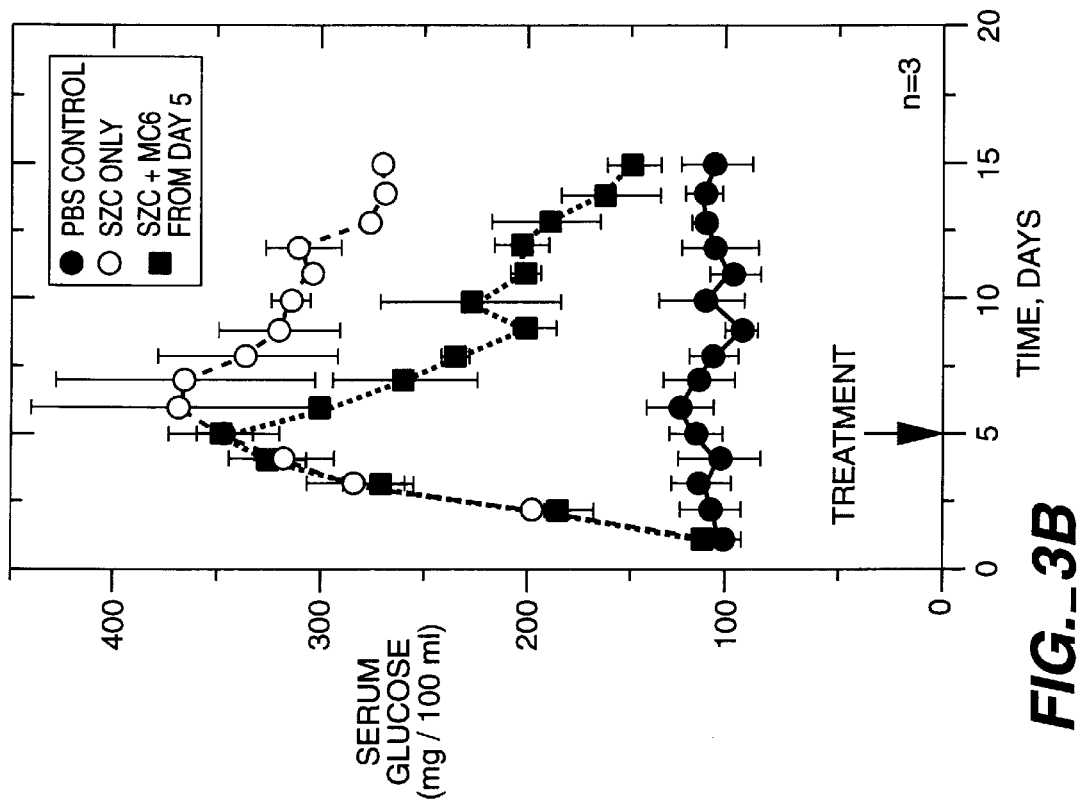
FIG._3B
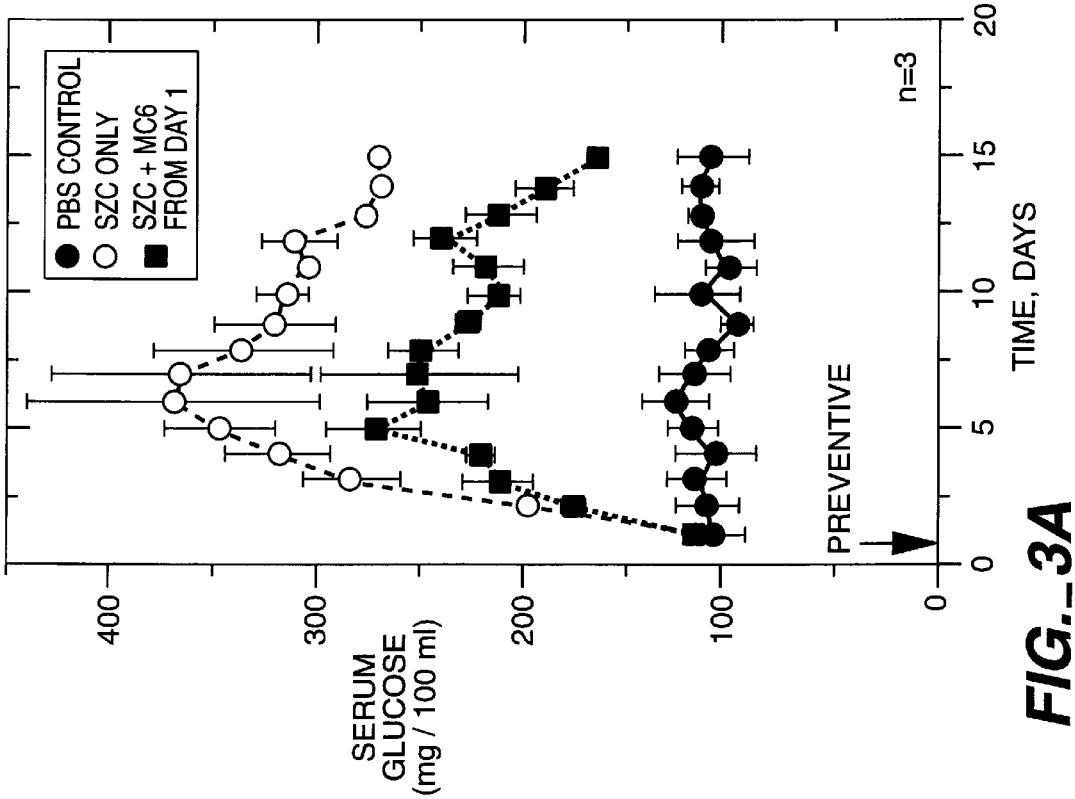
FIG._3A

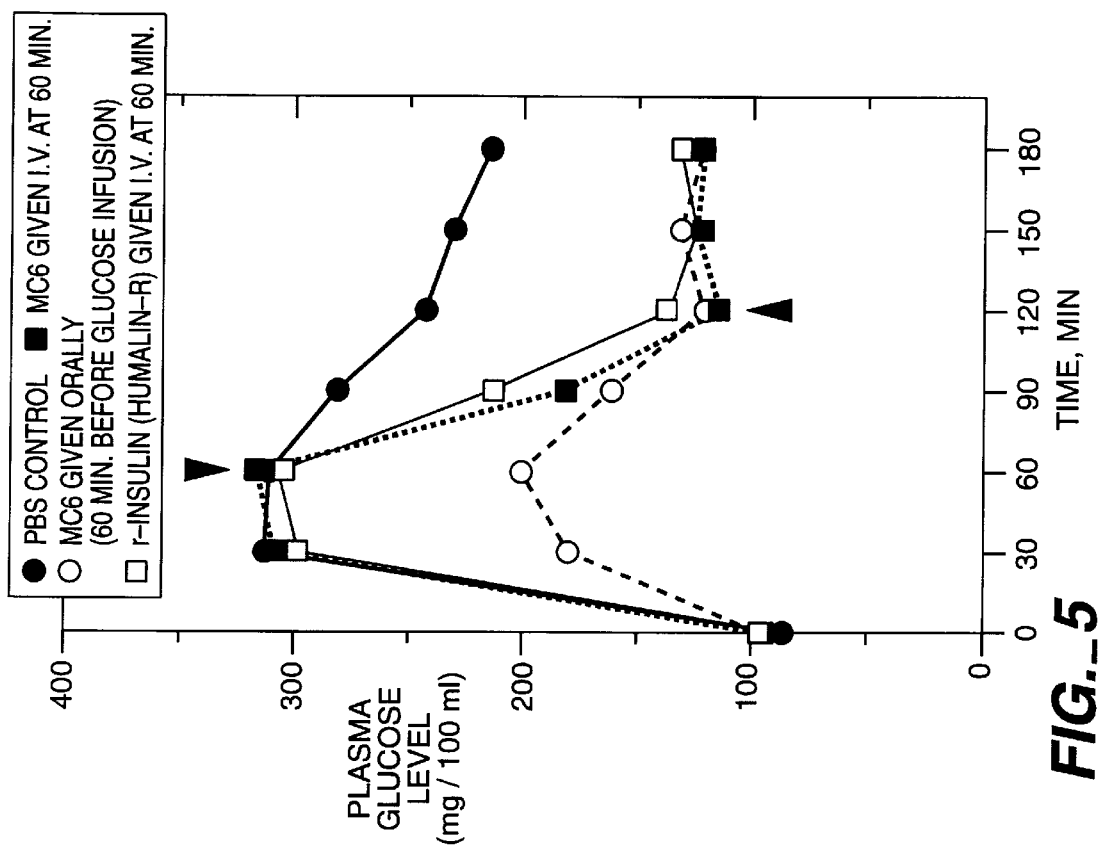
FIG._5
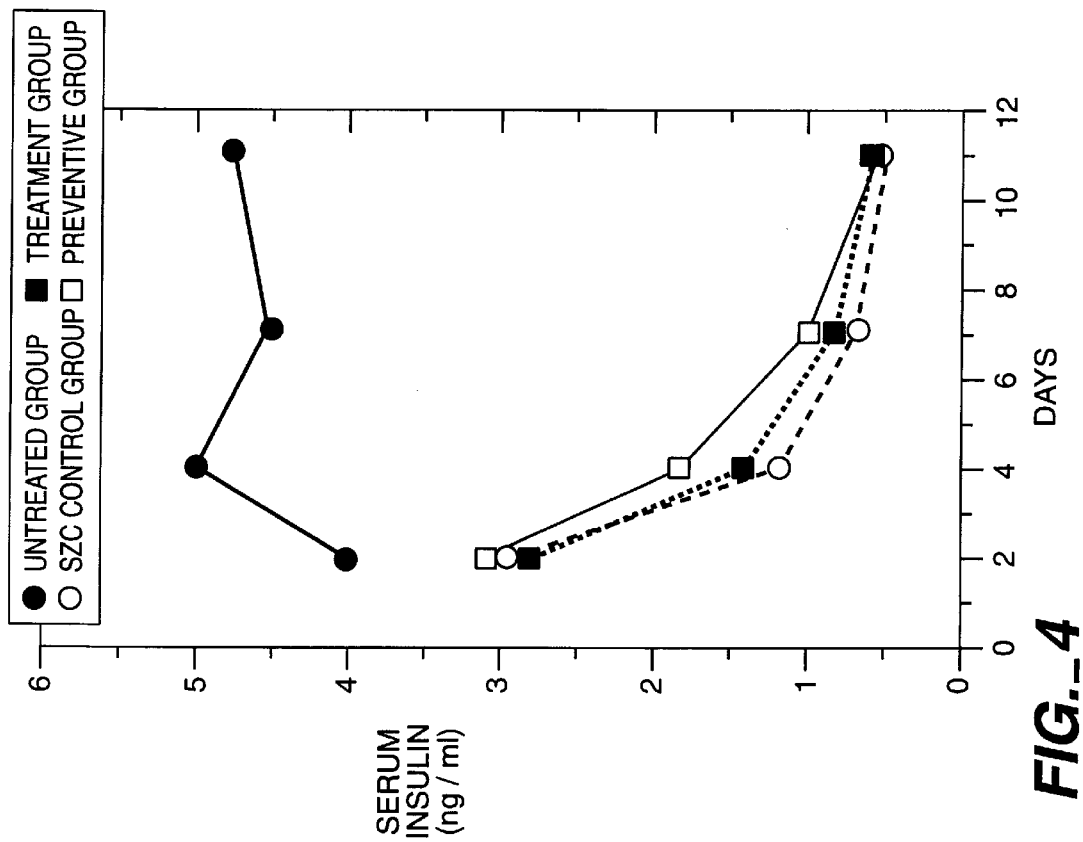
FIG._4

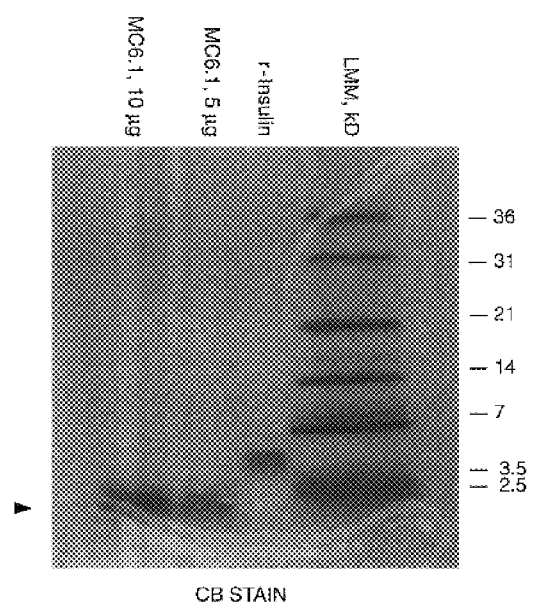
CB STAIN
FIG._6A
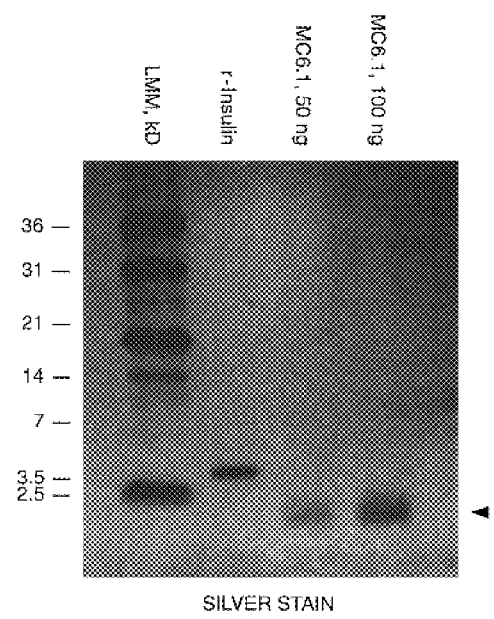
SILVER STAIN
FIG._6B

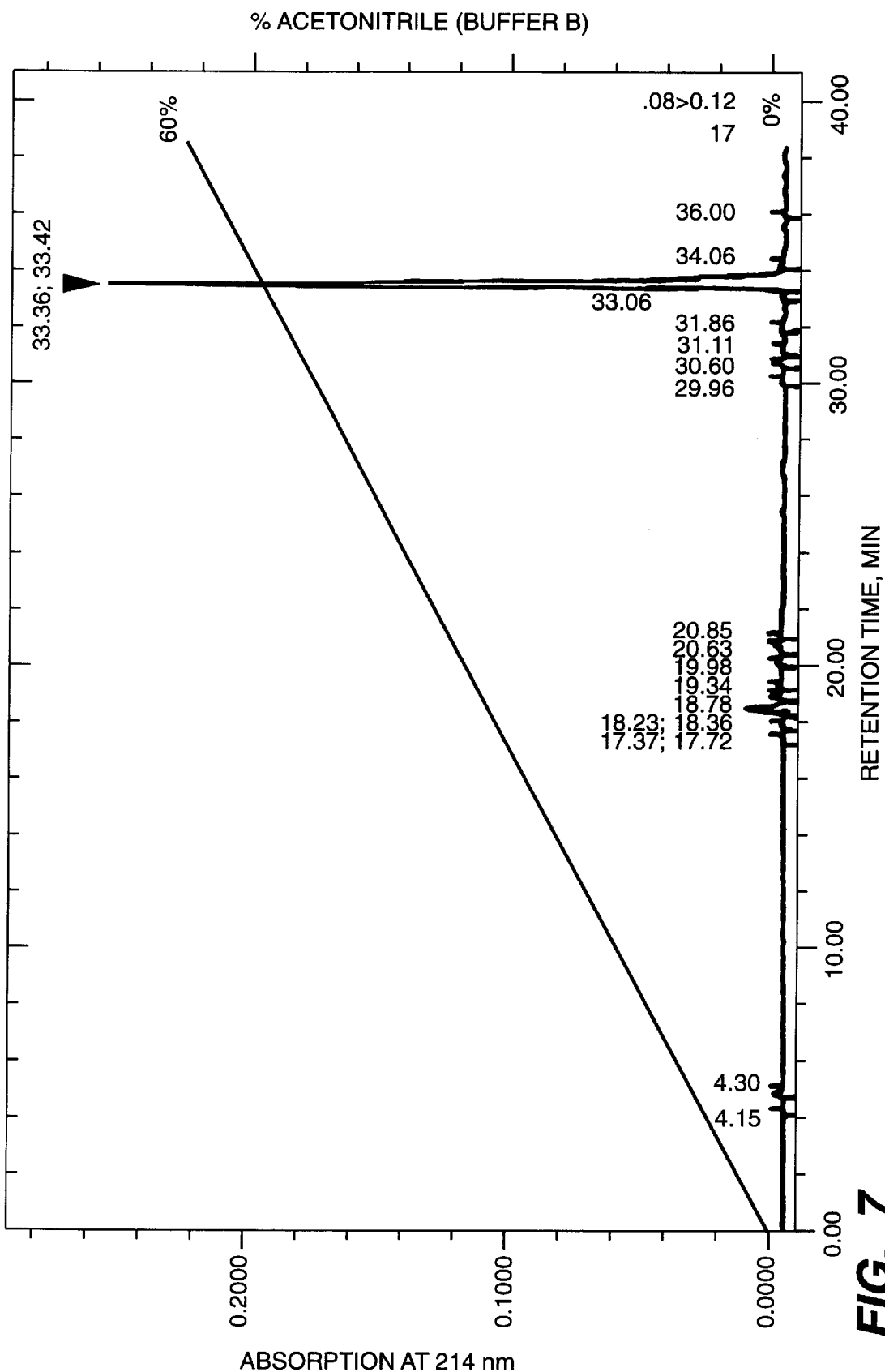
FIG._7

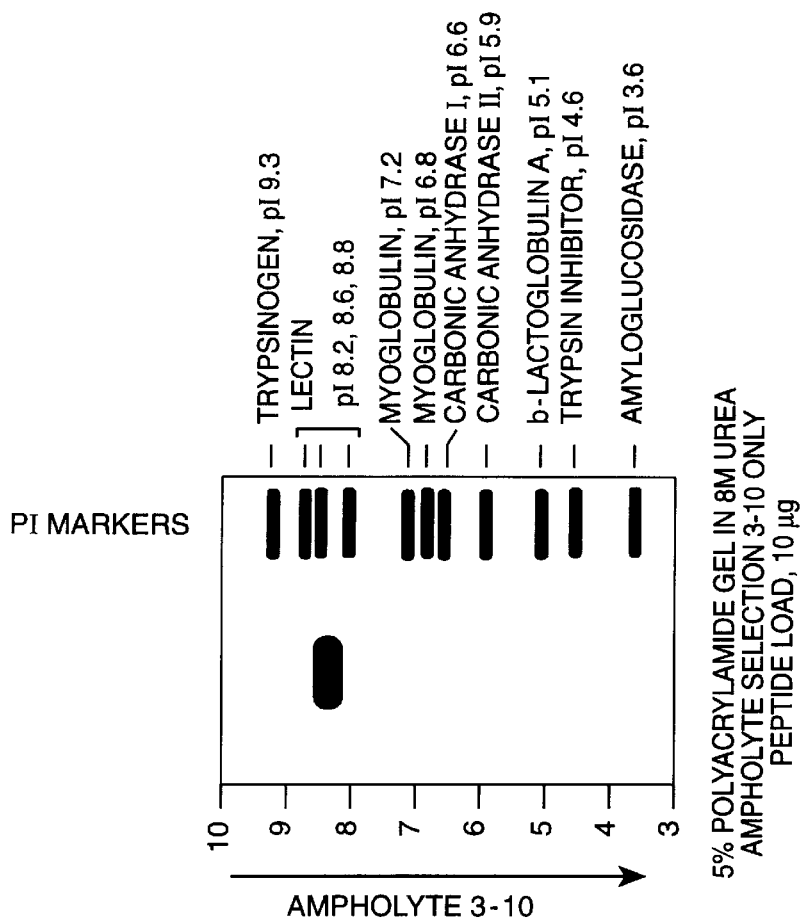
FIG._8B
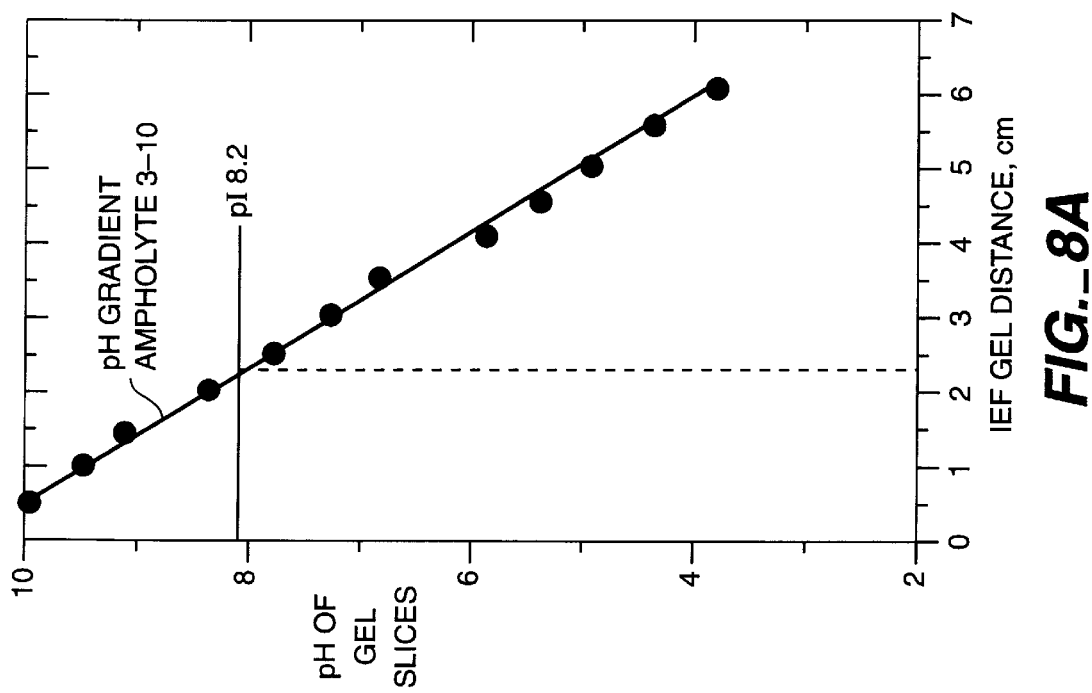
FIG._8A

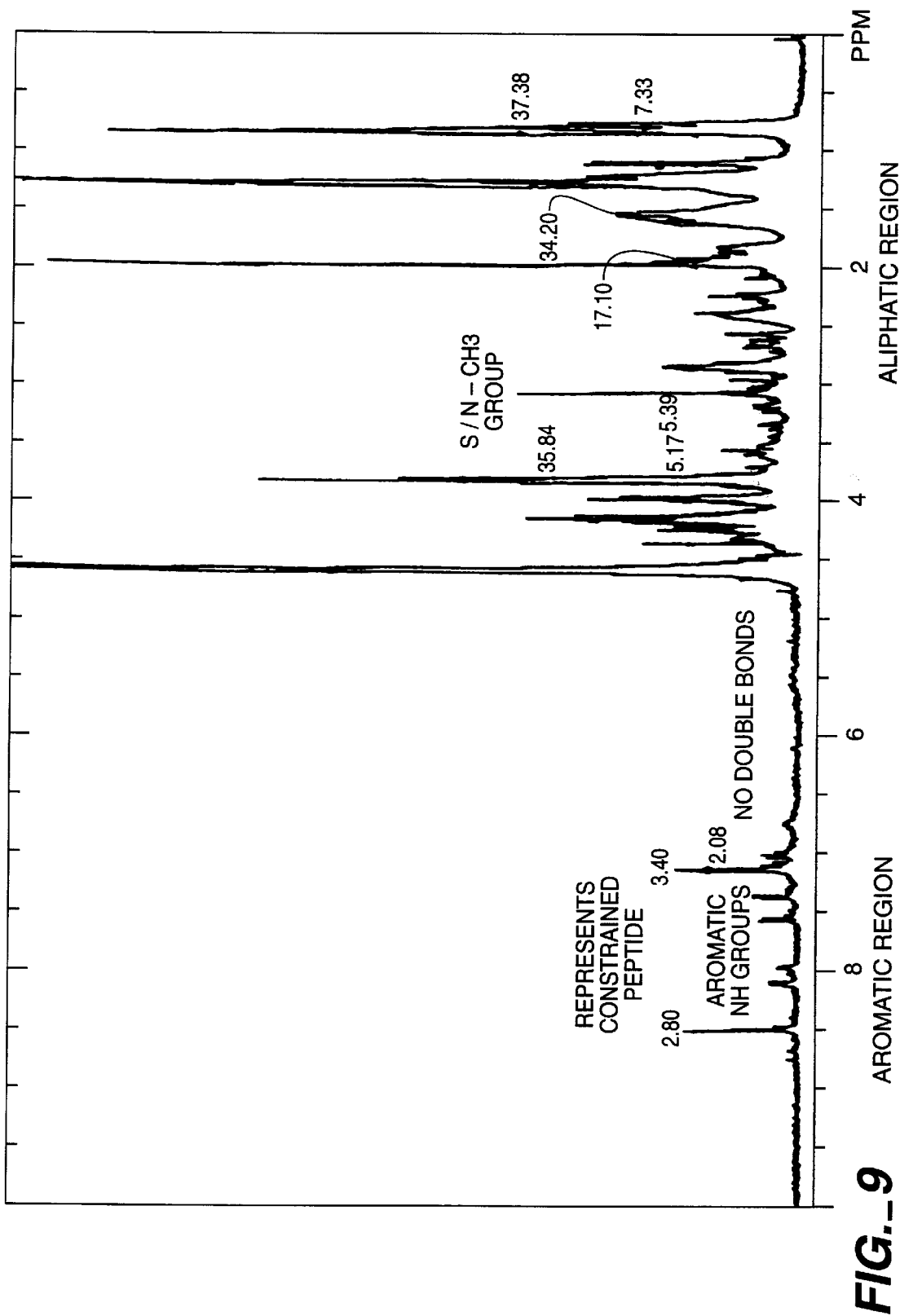
FIG._9

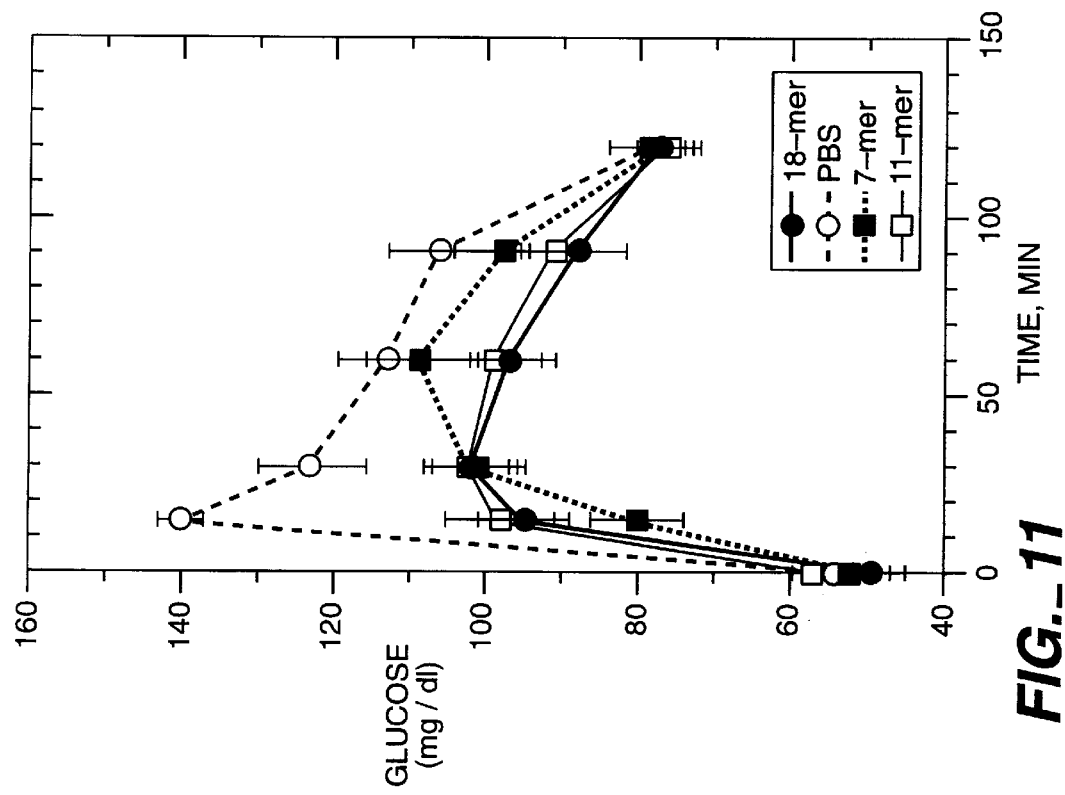
FIG._11
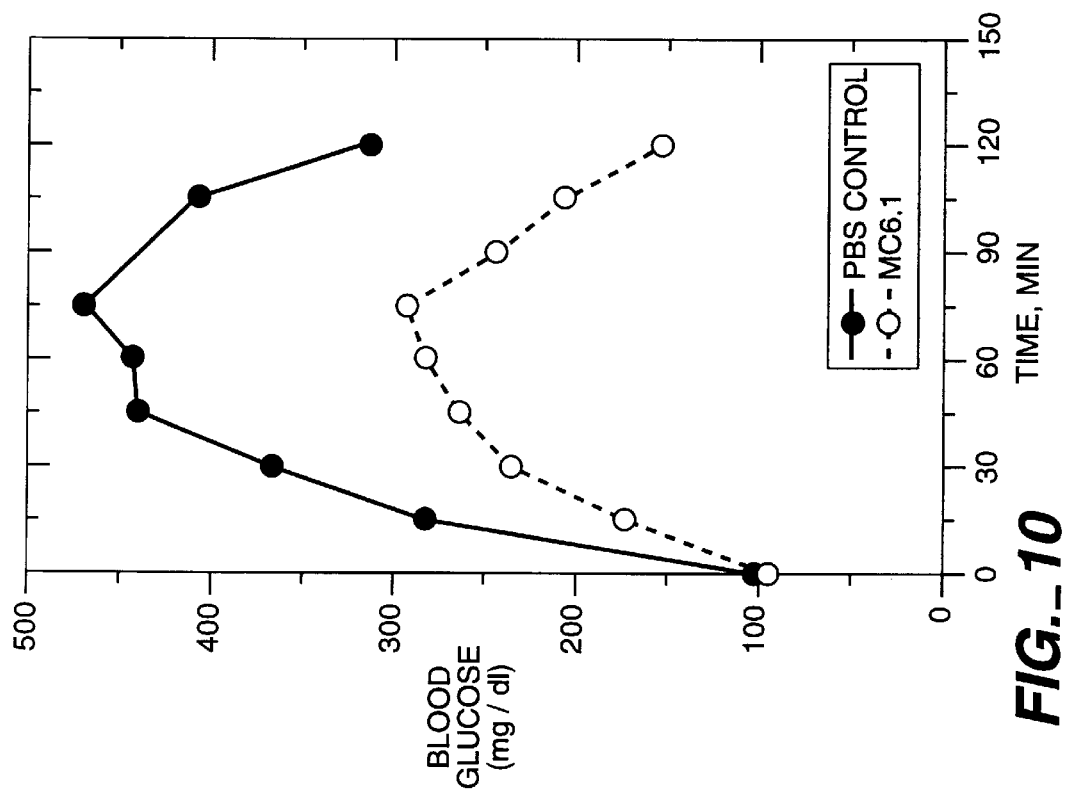
FIG._10

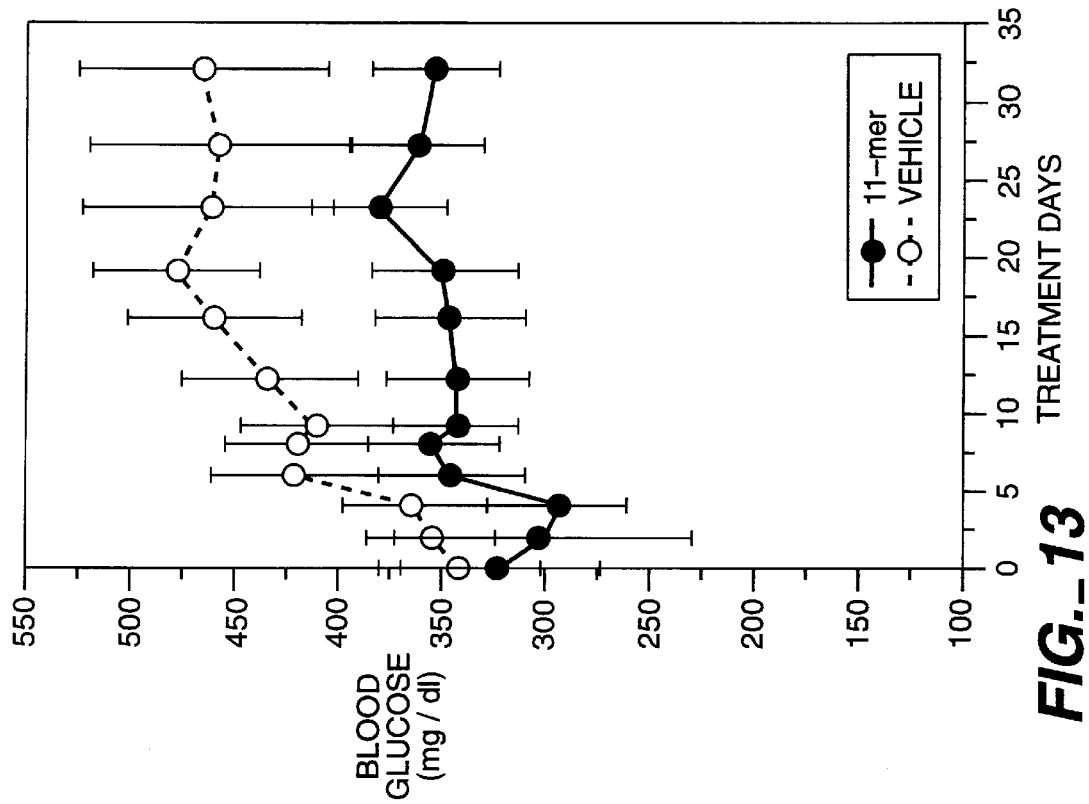
FIG._13
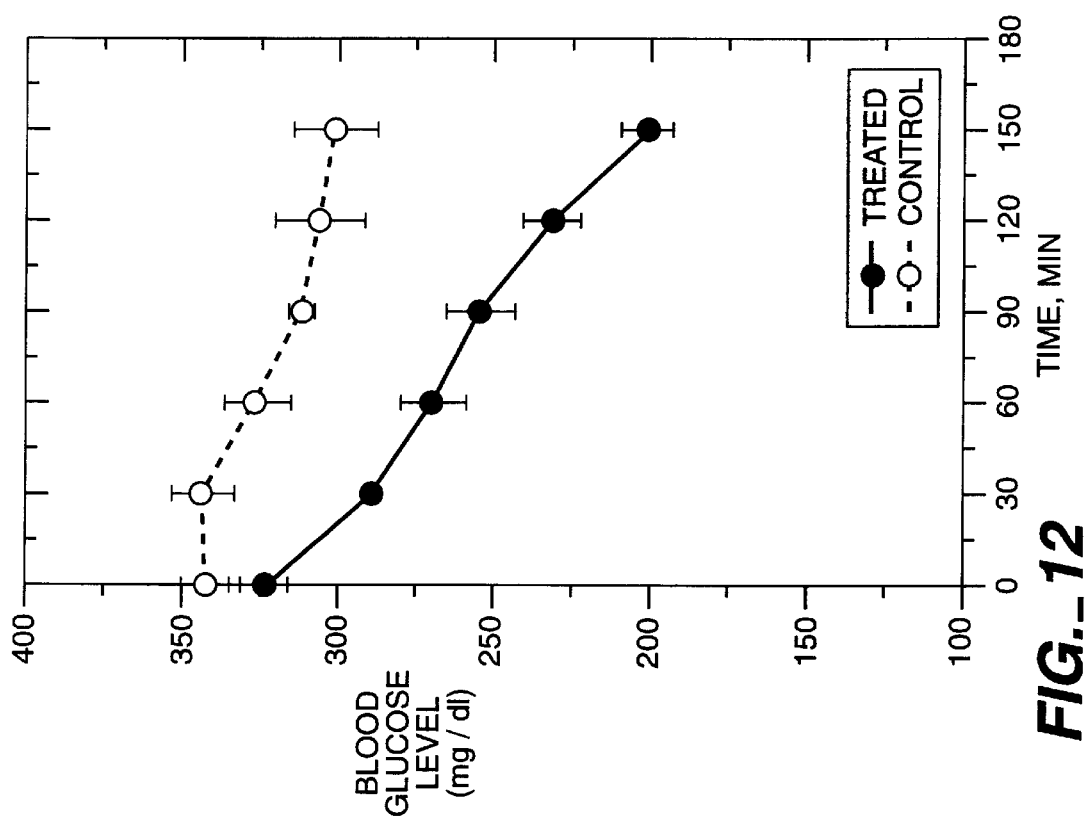
FIG._12

ORALLY ACTIVE FRACTION OF MOMORDICA CHARANTIA, ACTIVE PEPTIDES THEREOF, AND THEIR USE IN THE TREATMENT OF DIABETES

CROSS REFERENCE TO RELATED APPLICATIONS

This is a continuation-in-part of U.S. Ser. No. 08/850,855, filed May 2, 1997, abandoned which is a continuation-in-part of U.S. Ser. No. 08/831,039, filed Apr. 1, 1997, abandoned both incorporated by referenced in their entirety herein.

TECHNICAL FIELD

The field of this invention is diabetes.

BACKGROUND OF THE INVENTION

Non insulin dependent diabetes mellitus (NIDDM or Type II) is the fourth-leading cause of death in the United States and affects from 5 to 7% of the total world population, with an increasing prevalence in western countries. In diabetes, the body either does not produce enough insulin or the insulin which is produced is not effective, resulting in increased blood glucose level, a condition technically known as hyperglycemia. Although diabetes can affect people of any age, the majority of diabetics are over 45 years old. The disease tends to run in families, and the risk factor of acquiring the disease increases in overweight individuals.

Diabetes is a chronic disease with no cure and is linked with several other disorders. It is the leading cause of blindness in people ages 25–74. Ten percent of all people with diabetes develop kidney disease. Diabetes is the most frequent cause of non-traumatic lower limb amputation. The risk of leg amputation is 30 times greater for people with diabetes. People with diabetes are two to four times more likely to develop heart diseases, and are five times more likely to suffer from stroke.

The cause of diabetes is still a mystery, although both genetics and environment appear to play a role. There are two types of diabetes: Insulin dependent (Type I) and Non-insulin dependent (Type II). Type I diabetes is an autoimmune disease frequently occurring in children and young adults. The autoantigen responsible for triggering Type I diabetes is still unknown and patients have to take i.v. insulin daily to survive for their life.

Type II diabetes is a metabolic disorder resulting from the body's inability to make a sufficient amount of insulin or to properly use the insulin that it does produce, and is considered the most common form of the disease. Although insulin secretion and insulin resistance are considered the major defects, the precise genetic factors involved remain unknown. Patients with diabetes usually have one or more of the following defects. These are: less production of insulin by the pancreas; oversecretion of glucose by the liver; impairment of glucose uptake by the skeletal muscle; defects in glucose transporters (Glut-1, Glut-4); desensitization of insulin receptors; and defect in the metabolic breakdown of polysaccharides.

The current therapy utilizes four classes of oral hypoglycemic agents besides i.v. insulin. These are summarized below:

| Class | Approved Drugs | Mechanisms of Action | Limitations |
|---|---|---|---|
| Sulfonylureas | 4 (1st gen.) 2 (2nd gen.) | Acts on pancreas to release more insulin | Resistance development |
| Biguanides | Only one (metformin) | Reduces glucose secretion by liver. Also improves insulin sensitivity. | Liver problem Lactic acidosis |
| α-Glucosidase Inhibitor | Only one (acarbose) | Interferes with digestive process. Reduces glucose absorption. | Only at postprandial level. |
| Thiazolidine-dione | Only one (troglitazone) | Reduces insulin resistency | "Add-on" with insulin Not for people with heart and liver disease. |

As is apparent from the above table, each of the current agents available for use in the treatment of diabetes has certain disadvantages. Accordingly there is continued interest in the identification and development of new agents for use in the treatment of diabetes.

*M.charantia* is a tropical plant whose fruits are used as a vegetable. Several groups have reported on the hypoglycemic activity of *M.charantia*, both in mammal models (Shibib et al., Biochem. J., 292, 267–270 (1993); Ali et al., Planta Med. 59, 408–412 (1993); Akhtar et al., Planta Med. 42, 205–212 (1981)) and in humans (Leatherdale et al., Br. Med. J. 282, 1823–1824 (1981); Aslam et al., Lancet, I. 607 (1979)). However, the hypoglycemic component and the mechanism of action remains unknown.

The isolation of an 11 kDal peptide obtained from *M.charantia* having insulin like activity is reported in: Khanna et al., "Hypoglycemic Activity of Polypeptide-p from a Plant Source," 20th Annual Meeting of the American Society of Pharmacology, Purdue University, West Lafayette, Jul. 29–Aug. 3, 1979; Baldwa et al., Upsala J. Med. Sci. (1977) 82:39–41 and U.S. Pat. No. 3,945,988. In all of these reports, the insulin like polypeptide was non-orally administered, e.g. i.v. or subcutaneously.

A recent report indicates that the crude alcoholic extract of *M.charantia* lowers plasma glucose level partly by stimulation of glycogen synthesis in the liver and it is unlikely that it acts as an insulin secreting agent (Sarkar et al., Pharmacol. Res., 33, 1–4 (1996)).

SUMMARY OF THE INVENTION

A water soluble fraction of *M.charantia* (MC6) and methods for its preparation and use in the treatment of hyperglycemic disorders are provided. MC6 is characterized by migrating as a single band on SDS-PAGE electrophoresis having a molecular weight of less than 10 kDal, having a size smaller than recombinant insulin, comprising three peptides, and being free of high molecular weight protein contaminants. Also provided is a specific peptide component of MC6, labeled MC6.1 (SEQ ID No. 1), and peptide derivatives of MC6.1 (SEQ ID No. 1) which are shorter in length than MC6.1, MC6.2 (SEQ ID No. 2) and MC6.3 (SEQ ID No. 3), which exhibit hypoglycemic activity and may be administered orally to treat a variety of hyperglycemic disorders.

BRIEF DESCRIPTION OF THE FIGURES

FIG. 1A shows the results of gel electrophoresis on SDS-20%-PAGE of various water soluble fractions of M.charantia; FIG. 1B shows the purified MC6 preparations; and FIG. 1C shows the results of HPLC of MC6;

FIG. 2A is a graphical representation showing the effect of an unpurified aqueous extract of M.charantia and a control on plasma glucose levels over time in SD rats; FIG. 2B. is a graphical representation showing the effect of orally administered MC6 on blood glucose levels over time in SD rats;

FIGS. 3A & B provide graphical representations of the effect of MC6 on blood glucose levels in rats suffering from SZC induced diabetes;

FIG. 4 is a graphical representation demonstrating that oral administration of MC6 does not increase serum insulin level; and FIG. 5 is a graphical representation demonstrating that oral administration of MC6 is as effective as I.V. administration of r-insulin in reducing blood glucose levels.

FIGS. 6(a) & (b) show the results of SDS-PAGE analysis of MC6.1 (SEQ ID No. 1) in a 4–20% tris-glycine gradient gel using Coomassie Blue and Silver stain, respectively.

FIG. 7 provides a graphical representation of the results obtained from purification of MC6.1 using C18 RP-HPLC.

FIGS. 8a & b provide the results of isoelectric point analysis for MC6.1 (SEQ ID No. 1).

FIG. 9 provides the results of NMR analysis of MC6.1 (SEQ ID No. 1).

FIG. 10 provides a graphical representation of the effect of MC6.1 (SEQ ID No. 1) on blood glucose levels.

FIG. 11 provides a graphical representation of the hypoglycemic activity of MC6.1 (SEQ ID No. 1), 6.2 (SEQ ID No. 2) and 6.3 (SEQ ID No. 3) in oral glucose tolerance tests in normal rats.

FIG. 12 provides a graphical representation of the glucose lowering ability of MC6.2 (SEQ ID No. 2) in diabetic rats.

FIG. 13 is a graphical representation of the hypoglycemic effect of MC6.2 (SEQ ID No. 2) in non-obese diabetic mice.

DESCRIPTION OF THE SPECIFIC EMBODIMENTS

A water soluble fraction of M.charantia named MC6, an active peptide component thereof named MC6.1 (SEQ ID No. 1), and peptide derivatives thereof, MC6.2 (SEQ ID No. 2) and MC6.3 (SEQ ID No. 3), methods for their preparation and use in the treatment of hyperglycemic disorders are provided. MC6 is characterized by comprising three peptides that move together as a single band on SDS-PAGE with a molecular weight of 10 kDal and has a size smaller than recombinant insulin. MC6 and MC6.1 (SEQ ID No. 1) exhibit hypoglycemic activity and are orally active. In further describing the subject invention, the characteristics of MC6 and MC6.1 (SEQ ID No. 1) will be further described in greater detail, followed by a description of methods for its preparation and use in the treatment of hyperglycemic disorders, particularly in the treatment of humans suffering from diabetes.

The derivatives, MC6.2 (SEQ ID No. 2) and MC6.3 (SEQ ID No. 3) are, respectively, 11-a.a. and 7-a.a. peptide derivatives of the 18-a.a. peptide, MC6.1 (SEQ ID No. 1).

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

MC6 of the subject invention is a water soluble fraction or extract of the plant species M.charantia. Although MC6 may be derived from one or more tissues or components of the M.charantia, including the leaves, stems, roots, fruit, seeds and the like, including the whole M.charantia plant, MC6 is usually derived from M.charantia fruit, preferably unripe M.charantia fruit that has been separated from seeds.

MC6 is characterized by moving as a single band on SDS-20% PAGE, where the molecular weight of the single band is less than 10 kDal, where the strength of the electric field applied during SDS-20% PAGE is 100 V. The MC6 has a size smaller than recombinant insulin, and is therefore less than about 6 kDal. MC6 is further characterized by eluting as three peaks following High Performance Liquid Chromatography (HPLC), where the conditions of HPLC are reverse phase on C8 or C18 columns. Under these conditions, the first peak elutes at 11.33 min, the second peak elutes at 25.35 min and the third peak elutes at 34.67 min.

The MC6 of the subject invention is a preparation free of high molecular weight contaminants, e.g. proteins, where high molecular weight contaminants is used in this application to denote molecules having a molecular weight in excess of about 50 kDal. Usually, the MC6 is free of any contaminants having a molecular weight in excess of 10 kDal.

MC6 exhibits hypoglycemic activity in mammals. By hypoglycemic activity is meant that upon administration of MC6 to the mammal, the blood glucose level of the mammal decreases, where the amount of decrease in the blood glucose level is proportional to the amount of MC6 administered to the mammal. MC6 exhibits hypoglycemic activity whether it is administered orally or intravenously, and thus is orally active or orally bioavailable, by which is meant that it is not inactivated by passing from the gastrointestinal tract into the mammal.

The MC6 may be prepared using any convenient means which provide for separation of the MC6 from the source M.charantia tissue. One means of obtaining MC6 from M.charantia tissue is to first make a raw suspension of the tissue by macerating the tissue in the presence of a solvent, e.g. phosphate buffered saline (PBS), water and the like, where maceration may be accomplished using a blender or other maceration means. The particulate matter of the resultant suspension is then separated and discarded from the liquid phase, where this step may be accomplished by centrifuging, usually at a speed between about 10,000 and 16,000 rpm, followed by filtration of the supernatant, where filtration will generally be through filters having pore sizes ranging from 0.5 to 0.10 μ, usually from about 0.45 to 0.22 μ, where the filtration may be under vacuum. The resultant filtrate is then passed sequentially through 30 kDal and 10 kDal cutoff membranes, where such membranes are known in the art and representative membranes include Amicon M.W. cut off filters, and the like, to obtain a water soluble fraction of the initial M.charantia tissue which contains MC6. The resultant water soluble fraction may be used as is or further processes for subsequent use, where further processing may include dehydration, e.g. lyophilization, and the like. The resultant water soluble fraction can also be stored in liquid form at from 1 to 5, usually 2 to 4° C. in the presence of preservatives, such as sodium benzoate, and the like.

MC6.1 (SEQ ID No. 1) is a specific peptide component of MC6 that migrates as a single band in SDS-PAGE analysis (4–20 % tris-glycine gradient gel) and has a molecular weight as determined by SDS-PAGE of less than 2.5 kD. MC6.1 (SEQ ID No. 1) has an isolectric point of 8.2. MC6.1 is 18 amino acid residues in length, where the amino acid sequence of MC6.1 is:

K-T-N-M-K-H-M-A-G-A-A-A-A-G-A-V-V-G (SEQ ID NO:01)

MC6.1 (SEQ ID No. 1) exhibits hypoglycemic activity in mammals. The MC6.1 (SEQ ID No. 1) of the present invention is MC6.1 which has been separated from its natural environment, e.g. is present in MC6, is in isolated or pure form, and the like.

Also provided are peptide analogues and mimetics of MC6.1 (SEQ ID No. 1) which exhibit hypoglycemic activity. The MC6.1 (SEQ ID No. 1) analogues and mimetics will comprise, as an active motif sequence, at least 8 amino acids, usually at least about 12 amino acids, more usually at least about 18 amino acids, and fewer than about 40 amino acids, more usually fewer than 30 amino acids. Specific peptides are MC6.2 (SEQ ID No. 2), an 11-a.a. derivative of MC6.1 (SEQ ID No. 1) having the sequence:

K-T-N-M-K-H-M-A-G-A-A (SEQ ID NO:02)

and a 7-a.a. derivative having the sequence:

K-T-N-M-K-H-M (SEQ ID NO:03)

It is understood that up to about three substitutions or deletions may be made in the subject sequences, where the change will not be more than about 20 number %, usually not more than about 10 number % of the number of amino acids in the active motif. Preferred are conservative substitutions, as known in the art, including substitutions within the large hydrophobic group: isoleucine, leucine, valine and phenylalanine; between serine and threonine; glycine and alanine; asparagine and glutamine; aspartic acid and glutamic acid; or lysine, arginine and histidine.

In addition to purification from its natural source, the MC6.1 (SEQ ID No. 1), as well as peptide analogues and mimetics thereof, such as MC6.2 (SEQ ID No. 2) and MC6.3 (SEQ ID No. 3), may be prepared in accordance with conventional techniques, such as synthesis (for example, use of a Beckman Model 990 peptide synthesizer or other commercial synthesizer). Peptides may be produced directly by recombinant methods (see Sambrook et al. *Molecular Cloning: A Laboratory Manual*, CSHL Press, Cold Spring Harbor, N.Y., 1989) or as a fusion protein, for example to a protein that is one of a specific binding pair, allowing purification of the fusion protein by means of affinity reagents, followed by proteolytic cleavage, usually at a site engineered to yield the desired peptide (see for example Driscoll et al. (1993) *J. Mol. Bio.* 232:342–350).

The oligopeptides (i.e. MC6.1, MC6.1 analogues, MC6.1 mimetics) may be extended to provide convenient linking sites, e.g. cysteine or lysine, to enhance stability, to bind to particular receptors, to provide for site-directed action, to provide for ease of purification, to alter the physical characteristics (e.g. solubility, charge, etc.), to stabilize the conformation, etc. The oligopeptides may be joined to non-wild-type flanking regions as fused proteins, joined either by linking groups or covalently linked through cysteine (disulfide) or peptide linkages. The oligopeptide may be linked through a variety of bifunctional agents, such as maleimidobenzoic acid, methyldithioacetic acid, mercaptobenzoic acid, S-pyridyl dithiopropionate, etc. The oligopeptides may be joined to a single amino acid at the N- or C-terminus of a chain of amino acids, or may be internally joined. For example, the subject peptides may be covalently linked to an immunogenic protein, such as keyhole limpet hemocyanin, ovalbumin, etc. to facilitate antibody production to the subject oligopeptides.

Alternatively, the subject oligopeptides may be expressed in conjunction with other peptides or proteins, so as to be a portion of the chain, either internal, or at the N- or C-terminus. Various post-expression modifications may be achieved. For example, by employing the appropriate coding sequences, one may provide farnesylation or prenylation, such that the subject peptide will be bound to a lipid group at one terminus, and will be able to be inserted into a lipid membrane, such as a liposome.

The subject oligopeptides may be PEGylated, where the polyethyleneoxy group provides for enhanced lifetime in the blood stream. The subject oligopeptides may also be combined with other proteins, such as the Fc of an IgG isotype to enhance complement binding, or with a toxin, such as ricin, abrin, diphtheria toxin, or the like, particularly the A chain. The oligopeptides may be linked to antibodies for site directed action. For conjugation techniques, see, for example, U.S. Pat. Nos. 3,817,837; 3,853,914; 3,850,752; 3,905,654; 4,156,081; 4,069,105; and 4,043,989, which are incorporated herein by reference.

MC6, MC6.1 (SEQ ID No. 1), MC6.2 (SEQ ID No. 2) and MC6.3 (SEQ ID No. 3) (as well as analogues and mimetics thereof) of the subject invention find use in the treatment of diseases characterized by the presence of elevated blood glucose levels, e.g. hyperglycemic disorders, such as diabetes mellitus, including both Type I and Type II diabetes, as well as other hyperglycemic related disorders, such as obesity, increased cholesterol kidney related disorders, and the like. By "treatment" is meant that the MC6, MC6.1 (SEQ ID No. 1), MC6.2 (SEQ ID No.2) and MC6.3 (SEQ ID No. 3) (as well as analogues and mimetics thereof) are administered to at least reduce the blood glucose level in the host suffering from the hyperglycemic disorder. In treating hyperglycemic disorders with MC6 and the subject oligopeptides, the MC6 or oligopeptides are administered to the host in an amount sufficient to reduce the blood glucose level in the host to an acceptable range, wherein acceptable range means ±10%, usually ±8%, and more usually ±5% of the normal average blood glucose level for the host.

A variety of hosts may be treated according to the subject invention to reduce their blood glucose levels, where such hosts are mammalian and include livestock, valuable or rare animals, pets, such as dogs and cats, and humans.

Of particular interest are methods of treating human hyperglycemic disorders, such as diabetes, including both Type I and Type II diabetes, where MC6, MC6.1 (SEQ ID No. 1), MC6.2 (SEQ ID No. 2), MC6.3 (SEQ ID No. 3) and analogues and mimetics thereof, are administered to the human suffering from the hyperglycemic disorder to at least reduce the blood glucose level of the human, where the blood glucose level is reduced to about the normal blood glucose range for the human. Although, the active agents may be administered to the human using any of the convenient techniques described above, of particular interest is the oral administration of active agents.

For therapy with the fraction MC6 or the MC6.1 (SEQ ID No. 1), 6.2 (SEQ ID No. 2) and/or 6.3 (SEQ ID No. 3)

peptides, the active compounds may be administered to the host suffering from the hyperglycemic disorder using any convenient administration technique, where such techniques include intravenous, intradermal, intramuscular, subcutaneous, oral, and the like, where oral routes of administration are of particular interest. The dosage delivered to the host will necessarily depend on the route by which the dosage is administered, but will generally range from about 50 to 500 mg/70 kb human body weight, usually from about 100 to 200 mg/70 kg human body weight. In treating human hyperglycemic disorders with MC6, the dosage of active fraction or compound administered to the human will generally range from about 50 to 500, usually from about 100 to 200 mg/70 kg of human body weight.

In using the active fraction or compounds according to the subject invention, they may be combined with a physiologically acceptable vehicle to produce a pharmaceutical composition. The nature of the physiologically acceptable vehicle with which the active fraction or compound is combined to produce the pharmaceutical composition will necessarily depend on the method by which the pharmaceutical composition is intended to be administered. Illustrative vehicles include water, e.g. sterile water for injection, saline, and the like. Of particular interest will be physiologically acceptable vehicles suitable for use in the oral administration. Such vehicles are known in the art and include water, e.g. deionized water; saline, e.g. phosphate buffered saline, lyophylized powder in the form of tablets and capsules, where such forms may include various fillers, binders etc., and the like. The amount of active ingredient present in the pharmaceutical composition will be selected in view of the method by which the pharmaceutical composition is to be administered, and may be determined empirically by those of skill in the art.

For therapy, MC6.2 (SEQ ID No. 2) and/or MC6.3 (SEQ ID No. 3), and oligopeptide analogues or mimetics thereof may be administered orally, topically or parenterally, e.g. by injection at a particular site, for example, subcutaneously, intraperitoneally, intravascularly, intranasally, transdermally or the like. Formulations for oral administration include those listed above suitable for use with MC6. Formulations for injection will comprise a physiologically-acceptable medium, such as water, saline, PBS, aqueous ethanol, aqueous ethylene glycols, or the like. Water soluble preservatives which may be employed include sodium bisulfite, sodium thiosulfate, ascorbate, benzalkonium chloride, chlorobutanol, thimerosal, phenylmercuric borate, parabens, benzyl alcohol and phenylethanol. These agents may be present in individual amounts of from about 0.001 to about 5% by weight and preferably about 0.01 to about 2%. Suitable water soluble buffering agents that may be employed are alkali or alkaline earth carbonates, phosphates, bicarbonates, citrates, borates, acetates, succinates and the like, such as sodium phosphate, citrate, borate, acetate, bicarbonate and carbonate. Additives such as carboxymethylcellulose may be used as a carrier in amounts of from about 0.01 to about 5% by weight. The formulation will vary depending upon the purpose of the formulation, the particular mode employed for modulating the receptor activity, the intended treatment, and the like. The formulation may involve patches, capsules, liposomes, time delayed coatings, pills, or may be formulated in pumps for continuous administration. The specific dosage can be determined empirically in accordance with known ways. See, for example Harrison's, Principles of Internal Medicine, 11th ed. Braunwald et al. ed, McGraw Hill Book Co., New York, 1987.

Generally, a therapeutically effective dose of the active fraction or peptides, analogues and mimetics thereof, will be in the range of about 0.005–10, more usually from about 0.01–1 mg/kg of host weight. Such a dose will be sufficient to achieve the desired hypoglycemic activity. Administration may be as often as daily; usually not more than one or more times daily, or as infrequent as weekly, depending upon the level of drug which is administered. The amount oligopeptide administered will generally be adjusted depending upon the half life of the peptide, where dosages in the lower portion of the range may be employed where the peptide has an enhanced half life or is provided as a depot, such as a slow release composition comprising particles, introduced in a matrix which maintains the peptide over an extended period of time, e.g., a collagen matrix, use of a pump which continuously infuses the peptide over an extended period of time over a substantially continuous rate, or the like. Heller, *Biodegradable Polymers in Controlled Drug Delivery*, in: CRC Critical Reviews in Therapeutic Drug Carrier Systems, Vol. 1, CRC Press, Boca Raton, Fla., 1987, pp 39–90, describes encapsulation for controlled drug delivery, and Di Colo (1992) *Biomaterials* 13:850–856 describes controlled drug release from hydrophobic polymers.

The following examples are offered by way of illustration and not by way of limitation.

EXAMPLE 1

A. Isolation and Purification of the Active Component of *Momordica Charantia* Extract Fresh unripe fruits *Momordica Charantia* were washed, wiped and the seeds were removed. The pulp was blended in either phosphate buffered saline (PBS) or in deionized water. The suspension was centrifuged at 12,000×g and filtered through 0.22 μ sterile filters (obtained from Whatman) under vacuum. The clear supernatant was passed sequentially through 30 kD, 10 kD and 3 kD cut-off membranes obtained from Amicon filtration. 0.45 μ (1st step), 0.22 μ (2nd step) and 10 kD (3rd step) cut-off fractions were analyzed by SDS-20% polyacrylamide gel, and the results are provided in FIG. 1A. The 3rd step purified fraction showed a single band with a size smaller than human insulin. It is evident from the gel analysis that the purified fraction is free of various high molecular weight protein bands. Several batches of 10 K cut-off fraction labeled MC6 were purified in gram quantities, as shown in FIG. 1B. The resultant purified fractions were lyophilized to obtain MC6 free of uncombined water.

100 to 500 mg of the lyophilized MC6 was subjected to high performance liquid chromatography (HPLC)(reverse phase HPLC using TFA/acetonitrile linear gradient using C8 or C18 column (analytical)) and the results are provided in FIG. 1C. The HPLC analysis showed three major peaks with retention time of 17.35, 25.35 and 34.67 minutes respectively, demonstrating that MC6 comprises 3 peptides.

B. Hypoglycemic Activity of MC6

The hypoglycemic effect of purified fraction was compared with the starting crude extract preparation. SD rats (200 gram avg. obtained from Charles River, Mass.) were starved for 3 hours and an aliquot of blood was collected from the tail vein for measuring the basal plasma glucose level. 5 ml crude extract preparation or 1 ml of purified fraction MC6 (500 μg) in PBS (as prepared in Part A above) was administered orally to each rat. Control animals received an equal volume of PBS. Rats were anesthetized using suritol (i.p.)(0.08 μg/ml/kg, propanolol (1.7 μg/min/kg)). The jugular vein of each rat was cannulated and glucose was infused (18 mg/min/kg body weight) in 5 mM KCl and 140 mM NaCl solution for 3 hours. Blood was collected from the carotid artery at 30, 60, 90, 150 and 180 minutes. The plasma glucose level was estimated by the established calorimetric methods described in Kadish et al., Clin. Chem. (1968) 14: 116.

The results are presented in FIG. 2A. The results demonstrate that animals given crude extract have a significant decrease in blood glucose level at all points, the effect being substantially high at 60 minutes (with a relative difference of almost 100%). In parallel, as shown in FIG. 2B, a 1 ml aqueous purified fraction of MC6 (500 μg) in PBS given orally has an effect similar to the crude extract, suggesting that the isolated polypeptide pool of MC6 is the major active ingredient in the crude extract.

C. Effect of MC6 on preventive and treatment modes

The next set of experiments was carried out to demonstrate the efficacy of the purified fraction in both the preventive and the treatment modes of diabetes in animal model. Diabetes was induced in male SD rats (200–225 g each) using streptozotocin (40 mg/kg body weight) (obtained from Sigma Chem., MO). In the preventive model, animals received orally 1 ml (500 μg) of the purified fraction MC6 daily effective day 0. In the treatment model, animals received orally 1 ml of purified fraction MC6 (500 μg) at the onset of the disease on day 5. Serum glucose levels were monitored daily for a 15-day period. As shown in FIG. 3A and 3B, purified fraction MC6 is highly effective in both preventive and treatment modes ($p<0.001$ at day 10).

The effect of MC6 in the preventive mode of streptozotocin-induced diabetes strongly supports the suitability of using MC6 in treating Type I autoimmune diabetes as well.

D. Effect of MC6 on Serum Insulin Level

Serum insulin levels of animals at different days from the experiment described in Part C were measured to examine the role of MC6 in the regulation of the systemic insulin during the hypoglycemic effect. The quantitative measurement of serum insulin level was carried out by radioimmuno assay (LINKO assay) as described in Hales & Randle, Biochem. J. (1963) 88:137. FIG. 4 shows that oral administration of this fraction had no effect on enhancing the serum insulin level, suggesting that the effect of this fraction is not mediated through insulin secretion by the pancreas. In FIG. 4, Diabetes was induced with streptozotocin. The untreated group was given PBS only; the SZC group was given 40 mg/kg SZC; the preventative group was give MC6 orally from day 1; and the treatment group was given MC6 from day 5. Insulin was measured by standard RIA. The data represent average of triplicate determination.

E. Oral Administration of MC6 is Equally Effective as Systemic Injection of Insulin In the next experiment, orally administered purified fraction MC6 (500 μg) was compared with i.v. injection of insulin (150 mU) in SD rats. Animals were divided into four groups and starved for three hours. Group 1 received PBS only; group 2 was given MC6 orally 60 minutes before glucose infusion; group 3 received 150 mU r-insulin (Humalin-R® of Novo-Nordisk) i.v. at 60 minutes following glucose infusion through jugular vein and group 4 received 500 μg MC6 in 1 ml PBS (i.v.) at 60 minutes following glucose infusion through jugular vein. In all cases, glucose infusion was at 18 mg/min/kg. Blood samples were collected from the carotid artery at different time intervals and quantitative plasma glucose levels were measured calorimetrically.

The results are presented in FIG. 5. The results show that oral administration of MC6 is comparable to i.v. injection of r-insulin at 120 minute time period. Furthermore, systemic injection of this fraction and r-insulin showed identical hypoglycemic profile. These results demonstrate that the purified fraction is effective orally and systemically.

F. Characterization MC6.1 (SEQ ID No. 1)

MC6.1 was further characterized by SDS-PAGE analysis on 4 to 20% tris-glycine gradient gel using either coomassie blue or silver stain for visualization of resolved bands. The results are provided in FIGS. 6a and 6b.

G. Further Purification of MC6.1

MC6.1 was further purified and analyzed by C-18 RP HPLC (gradient 0.1% TFA buffer A; 60 % AcN in 0.1% TFA. The results are provided in FIG. 7.

H. Isolectric Point of MC6.1

The isolectric point of MC6.1 was analyzed and found to be 8.2. The results are provided in FIGS. 8a and 8b I. NMR Analysis of MC6.1

Proton NMR analysis was made of MC6.1 and the results are provided in FIG. 9.

J. Hypoglycemic Activity of MC6.1

The hypoglycemic activity of MC6.1 was assayed in a manner analogous to Example B. above. SD male rats weighing on average 220 g were used. The rats were orally given 50 μg MC6.1 in 500 μl. Control rats were administered PBS. The results are provided in FIG. 10. The results demonstrate the MC6.1 exhibits hypoglycemic activity following oral administration.

EXAMPLE 2

FIG. 1 represents the hypoglycemic activity of MC6.1 and its derivators, MC6.2 (SEQ ID No. 2) and 6.3 (SEQ ID No. 3) analogs in oral glucose tolerance test in normal rats. All three peptides were effective in lowering blood glucose in this experiment as compared to vehicle treated animals.

Glucose lowering ability of MC6.2 (SEQ ID No. 2) (11-amino acid peptide) was further evaluated in diabetic rats. Streptozotocin at a dose of 40 mgtkg body weight was injected in SD rats of average 200 g. As shown in FIG. 12, oral treatment of diabetic rats (average blood glucose 330 mg/dl) with MC6.2 at a dose of 100~g/rat (0.5 mg/kg body weight) lowered the blood glucose level by significantly as compared to the control group.

The hypoglycemic effect of MC6.2 (SEQ ID No. 2) (11-amino acid peptide) was evaluated in the treatment mode in non-obese diabetic (NOD) mice. As shown in FIG. 13, oral administration of MC6.2 in NOD mice daily has significant effect on blood glucose level as compared to vehicle treated animals.

These results demonstrate that the N-terminal 7–11 amino acid residues of MC6.1 (SEQ ID No. 1) are important for reducing blood glucose level which is useful for the development of therapeutics for the treatment of human diabetes.

It is evident from the above results and discussion that a novel extract of *M.charantia* and specific peptide agents are provided that are useful in the treatment of hyperglycemic disorders, particularly diabetes. Since the active agents of the invention do not cause an upregulation in the amount of insulin produced by the body, they provide a useful alternative mechanism for regulating blood glucose levels. Furthermore, since the MC6 and the peptide MC6.1, 6.2 (SEQ ID No. 2) and 6.3 (SEQ ID No. 3) are orally active, they provide significant advantages over conventional insulin products that have been used in the treatment of diabetes which must be introduced by more invasive and less convenient means of administration, such as i.v.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

K-T-N-M-K-H-M-A-G-A-A-A-A-G-A-V-V-G (SEQ ID NO:01).

3. The peptide according to claim 1, consisting of the amino acid sequence:

K-T-N-M-K-H-M-A-G-A-A (SEQ ID NO:02).

4. The peptide according to claim 1, consisting of the amino acid sequence:

K-T-N-M-K-H-M (SEQ ID NO:03).

5. A pharmaceutical composition comprising an effective anti-hyperglycemic amount of a peptide selected from group

What is claimed is:

1. A peptide having anti-hyperglycemic activity selected from the group consisting of peptides respectively consisting of SEQ ID No. 1, SEQ ID No. 2, SEQ ID No. 3.

2. The peptide according to claim 1, consisting of the amino acid sequence:

consisting of peptides respectively consisting of SEQ ID No. 1, SEQ ID No. 2, SEQ ID No. 3, and mixtures of two or more of said peptides, in a physiologically acceptable vehicle.

* * * * *

```
                         SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
         (A) LENGTH: 18 amino acids
         (B) TYPE: amino acid
         (C) STRANDEDNESS: single
         (D) TOPOLOGY: linear (xi) SEQUENCE DESCRIPTION: SEQ ID NO:1:

Lys Thr Asn Met Lys His Met Ala Gly Ala Ala Ala Ala Gly Ala Val
 1               5                  10                  15

Val Gly (2) INFORMATION FOR SEQ ID NO:2:

(i) SEQUENCE CHARACTERISTICS:
         (A) LENGTH: 11 amino acids
         (B) TYPE: amino acid
         (C) STRANDEDNESS: single
         (D) TOPOLOGY: linear (xi) SEQUENCE DESCRIPTION: SEQ ID NO:2:

Lys Thr Asn Met Lys His Met Ala Gly Ala Ala
 1               5                  10

(2) INFORMATION FOR SEQ ID NO:3:

(i) SEQUENCE CHARACTERISTICS:
         (A) LENGTH: 7 amino acids
         (B) TYPE: amino acid
         (C) STRANDEDNESS: single
         (D) TOPOLOGY: linear (xi) SEQUENCE DESCRIPTION: SEQ ID NO:3:

Lys Thr Asn Met Lys His Met
 1               5
```